United States Patent [19]

Badono et al.

[11] Patent Number: 4,817,122
[45] Date of Patent: Mar. 28, 1989

[54] APPARATUS FOR RADIATION ANALYSIS

[75] Inventors: Shinji Badono; Masaki Komaru; Toshimasa Tomoda, all of Hyogo, Japan

[73] Assignee: Mitsubishi Denki Kabushiki Kaisha, Tokyo, Japan

[21] Appl. No.: 831,806

[22] Filed: Feb. 21, 1986

[30] Foreign Application Priority Data

Feb. 22, 1985 [JP] Japan .................................. 60-32904

[51] Int. Cl.$^4$ .......................................... G01N 23/203
[52] U.S. Cl. ........................................ 378/88; 378/82; 250/359.1
[58] Field of Search ................. 378/88, 86; 250/358.1, 250/359.1

[56] References Cited

U.S. PATENT DOCUMENTS

| 3,626,183 | 12/1971 | Berrey et al. .......................... 378/88 |
| 3,843,881 | 10/1974 | Barten, Jr. et al. .................... 378/88 |
| 4,037,099 | 7/1977  | Oda et al. ............................ 378/86 |
| 4,200,702 | 4/1980  | Fanger et al. . |
| 4,558,220 | 12/1985 | Evans .................................... 378/88 |

FOREIGN PATENT DOCUMENTS 57-1781  1/1982  Japan .

Primary Examiner—Janice A. Howell
Assistant Examiner—David P. Porta
Attorney, Agent, or Firm—Bernard, Rothwell & Brown

[57] ABSTRACT

An apparatus for determining the mass of each of the constituents of a substance to be measured, per unit volume of the same, is disclosed. The apparatus includes a detector disposed at the position to receive energy of back scattered photons produced by a radiation directed on a substance to be measured and systems of measurement, which are smaller in number by one than the kinds of the constituents under investigation, and the signal from the detector is processed for measuring intensity of the energy components unique to each of the constituents.

7 Claims, 1 Drawing Sheet

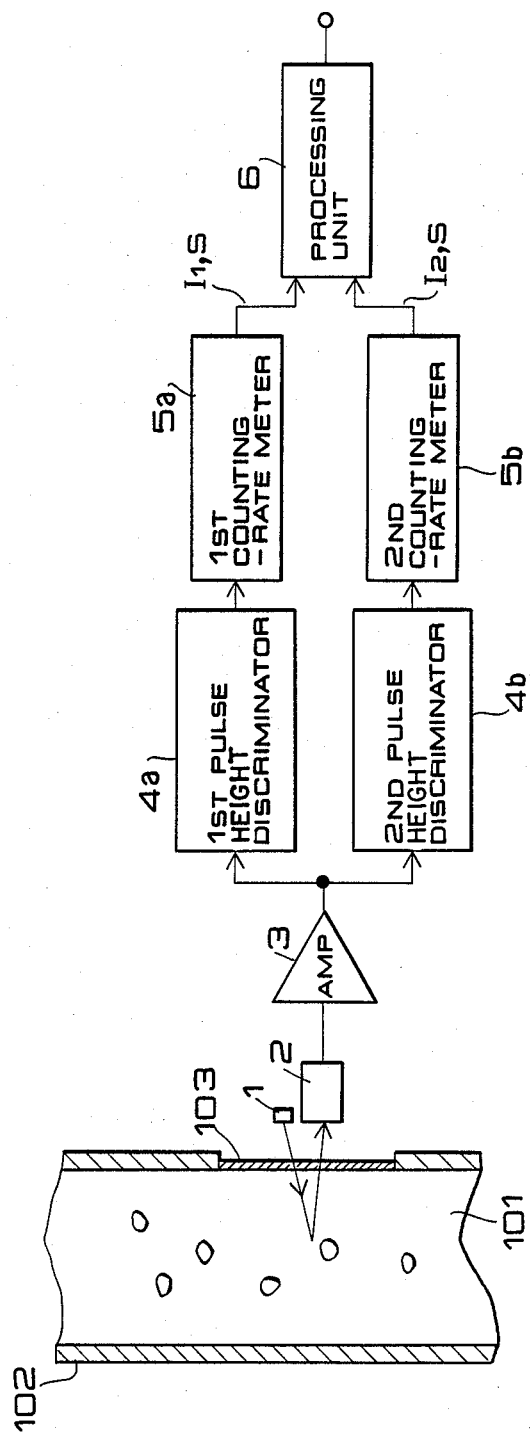

APPARATUS FOR RADIATION ANALYSIS

BACKGROUND OF THE INVENTION

1. Field of the Invention

The present invention relates to an apparatus for measurement of the mass of elements or molecules constituting an unknown compound or mixture.

2. Description of the Prior Art

The art of measuring the mass of more than two kinds of components (this number of kinds will hereinafter be referred to as "N" for convenience) constituting an unknown matter by the use of measured values of transmitted amount or scattered amount of radiation has already been well known to the public.

One of the apparatuses for radiation analysis of the described type was disclosed in Japanese Patent Application Publication No. 57-1781. Dealing with a substance to be measured including N kinds of elements, this well-known apparatus is constructed of N systems of radiation measurement which will differently respond to each of the elements and a linearization circuit which will compensate the responses made by these systems of radiation measurement and derive therefrom a linear combination of the mass of each component element per unit volume of the substance to be measured, wherein four-rule arithmetic computation is made based on the outputs from the linearization circuit so that the mass of each component element in the unit volume is computed. Further, other values, or properties, of the measured substance can also be obtained by computation from the mass of these component elements per unit volume.

The prior art apparatus will be described in more detail taking the case of the substance to be measured being composed of three kinds of elements. In the apparatus of the prior art, when the outputs of the linearization circuit are represented by $V_1$, $V_2$, and $V_3$, each value thereof can, with the mass of each element in the substance under measurement expressed by $X_1$, $X_2$, and $X_3$, be given by the following equations:

$$V_1 = K_1(a_{11}X_1 + a_{12}X_2 + a_{13}X_3)$$

$$V_2 = K_2(a_{21}X_1 + a_{22}X_2 + a_{23}X_3)$$

$$V_3 = K_3(a_{31}X_1 + a_{32}X_2 + a_{33}X_3)$$

where $K_1$, $K_2$, and $K_3$ are constants depending on the apparatus used, and $a_{11}$, $a_{12}$, $a_{13}$, $a_{21}$, $a_{22}$, $a_{23}$, $a_{31}$, $a_{32}$, and $a_{33}$ are constants determined by mutual actions between the component elements and the radiation.

$X_1$, $X_2$, and $X_3$ are generally obtainable from the above equations. However, to do so, it becomes necessary to provide systems of radiation measurement which are the same in number as the kinds of the component elements and which are different in their responses to respective component elements. This is true also of the case, for example, where the mass of each element per unit volume of the measured substance is to be determined, namely, then, it is necessary to provide systems for radiation measurement in the same number as the number of the component elements.

With the described prior art apparatus for radiation analysis, in such a case as mentioned above where $X_1/(X_1+X_2+X_3)$, $X_2/(X_1+X_2+X_3)$, $X_3/(X_1+X_2+X_3)$ are sought, the above three equations become necessary. This has required three kinds of systems for radiation measurement and has involved a problem that the apparatus becomes rather complex.

SUMMARY OF THE INVENTION

An object of the invention is to provide an apparatus for radiation analysis having a smaller number of systems for radiation measurement than the prior art apparatus as described above and therefore being of a simpler structure.

Another object of the invention is to provide an apparatus for radiation analysis which is able to measure, in a substance for measurement in which a plurality of compounds are uniformly mixed, the mass of each of the component compounds in a unit volume of the substance under measurement by the use of systems for radiation measurement which are smaller in number than the kinds of the component compounds.

The apparatus for radiation analysis according to the present invention is provided with systems for radiation measurement for measuring the component of the radiation of either X-ray or $\gamma$-ray that has been back scattered by the substance to be measured, the systems being smaller in number by one than the kinds of the components of the substance measured. The apparatus is further provided with a processing unit for providing the mass of each of the components in a unit volume of the substance to be measured through four-rule arithmetic computation of the signals proportional to the intensity of the back scattered radiation.

BRIEF DESCRIPTION OF THE DRAWINGS

A single drawing is a block diagram schematically showing an apparatus for radiation analysis according to the present invention.

DETAILED DESCRIPTION OF THE PREFERRED EMBODIMENTS

In the following there will be described the principle of measurement of mass of the components in a unit volume of the substance under measurement performed in the apparatus of the present invention through the use of the systems for radiation measurement which are smaller in number by one than the kinds of the components.

The radiation employed in the invention is either X-ray or $\gamma$-ray and the back scattering of the radiation is due to the Compton effect. When a radioactive ray passing through the substance to be measured is scattered at the surface of an element in an angle $\theta$ with reference to the angle of incidence, the energy $h\gamma'$ possessed by the scattered photon will, with the energy of the incident photon represented by $h\gamma$, be given by the following equation (1), which does not depend on the element itself as the target of the collision.

$$h\nu' = \frac{h\nu}{1 + \frac{h\nu}{m_0C^2}(1 - \cos\theta)} \quad (1)$$

where $m_0C^2$) represents the rest mass of an electron and is given by 511 KeV. Since scattering at the time $\theta = \pi$ is the back scattering, the energy $h\gamma'(\pi)$ of the back scattered photon is given by $$hv'(\pi) = \frac{hv}{1 + \frac{2hv}{m_0 C^2}} \quad (2)$$

and if the angle $\theta$ of scattering deviates from $\pi$, its energy becomes smaller than that expressed by the equation (2).

Then, since the probability of the Compton scattering is proportional to the number of electrons in the target, it depends on the components. The probability also depends on the energy of the incident photon.

The back scattering phenomenon due to a component consisting of two elements will be described in the following.

Loss of power, or attenuation, of the radiation passing through a substance to be measured is given by $\exp(-\mu\rho d)$, where d is the distance of the known transmission path. Therefore, the intensity $I(x)$ of the radiation transmitted to the depth of x in the substance to be measured and the intensity $I_S$ of the back scattered radiation reaching a radiation detector are expressed by the following equations (3) and (4), respectively:

$$I(x) = I_0 \exp[-\{\mu_1(E_0)\rho_1 + \mu_2(E_0) \cdot \rho_2\}x] \quad (3)$$

$$I_s = k \int_0^\infty I(x)\{\sigma_1(E_0)\rho_1 + \sigma_2(E_0)\rho_2\} \cdot \exp[-\{\mu_1(E_S)\rho_1 + \mu_2(E_S)\rho_2\}x]dx \quad (4)$$

where
$\rho$: mass density of substance
$\rho_1$: mass density of element 1
$\rho_2$: mass density of element 2
$E_0$: energy of photon of incident radiation
$E_S$: energy of photon of back scattered radiation
$I_0$: intensity of incident radiation
$\sigma_1(E_0)$: mass back scattering coefficient of element 1 to radiation having energy of photon $E_0$
$\sigma_2(E_0)$: mass back scattering coefficient of element 2 to radiation having energy of photon $E_0$
$\mu_1(E_0)$: mass absorption coefficient of element 1 to radiation having energy of photon $E_0$
$\mu_2(E_0)$: mass absorption coefficient of element 2 to radiation having energy of photon $E_0$
$\mu_1(E_S)$: mass absorption coefficient of element 1 to radiation having energy of photon $E_S$
$\mu_2(E_S)$: mass absorption coefficient of element 2 to radiation having energy of photon $E_S$
k: constant.

Substituting (3) in (4) and making the integration, we obtain the following equation (5):

$$I_s = kI_0 \frac{\sigma_1(E_0)\rho_1 + \sigma_2(E_0)\rho_2}{[\mu_1(E_0) + \mu_1(E_S)]\rho_1 + [\mu_2(E_0) + \mu_2(E_S)]\rho_2} \quad (5)$$

By arranging the equation (5) with reference to $\rho_1$ and $\rho_2$, $$\{kI_0\sigma_1(E_0) - I_S[\mu_1(E_0) + \mu_1(E_S)]\}\rho_1 + \quad (6)$$
$$\{kI_0\sigma_2(E_0) - I_S[\mu_2(E_0) + \mu_2(E_S)]\}\rho_2 = 0$$

Although the equation (6) is a linear equation with reference to $\rho_1$ and $\rho_2$, since the invariable term is zero, the ratio of $\rho_1$ to $\rho_2$ and hence the values of $$\frac{\rho_1}{\rho} = \frac{\rho_1}{\rho_1 + \rho_2}, \quad \frac{\rho_2}{\rho} = \frac{\rho_2}{\rho_1 + \rho_2}$$

can be obtained from the constants $\sigma$ and $\mu$ relative to the components and intensity of the incident radiation and the back scattered radiation $I_0$ and $I_S$.

Also, in the case where the number of components of the substance to be measured is three or more, the proportions of the components can similarly be obtained by the use of the systems of measurement of the back scattered radiation smaller in number by one than the components. The reason is that there exist such special conditions that the equation representing the back scattering is given in the form of a uniform linear equation with reference to $\rho i$ (i=1, 2, 3 ...) as in the equation (6) and the invariable term thereof becomes nil.

Now, the drawing showing the apparatus for radiation analysis of the invention will be described in the following. As an example, a compound consisting of hydrogen (H), carbon (C), and oxygen (O) is taken up as the substance to be measured by this apparatus.

Referring to the drawing, 101 denotes a fluid to be measured consisting of H, C, and O, which is flowing through a pipe 102, 103 denotes a radiation transmitting window formed of such light substance as beryllium, 1 denotes a radiation source of Am-241, 2 denotes a radiation detector of a pulse type, 3 denotes an amplifier for amplifying a signal from the radiation detector 2, 4a and 4b denote first and second pulse-height discriminators, respectively, for outputting pulses of a fixed height on receipt of pulses within a specific pulse-height range. Reference numerals 5a and 5b denote first and second counting-rate meters, respectively, for outputting a signal, such as a voltage signal, proportional to the frequency of the input pulses. Reference numeral 6 denotes a processing unit for determining the mass of the H, C, and O components in a unit volume of the substance to be measured through four-rule arithmetic computation by the use of the outputs from the two counting-rate meters 5a, 5b, the mass absorption coefficients $\mu_H(E_{1,0})$, $\mu_H(E_{2,0})$, $\mu_C(E_{1,0})$, $\mu_C(E_{2,0})$, $\mu_O(E_{1,0})$ and $\mu_O(E_{2,0})$ and the mass back scattered coefficients $\rho_H(E_{1,0})$, $\rho_H(E_{2,0})$, $\rho_C(E_{1,0})$, $\rho_C(E_{2,0})$, $\rho_O(E_{1,0})$ and $\rho_O(E_{2,0})$ for energy of first and second photons $(E_{1,0})$ and $E_{(2,0)}$ of hydrogen, carbon, and oxygen, and the mass absorption coefficients $\mu_H(E_{1,S})$, $\mu_H(E_{2,S})$, $\mu_C(E_{1,S})$, $\mu_C(E_{2,S})$, $\mu_O(E_{1,S})$ and $\mu_O(E_{2,S})$ for energy of back scattered photons $(E_{1,S})$ and $E_{(2,S)}$ corresponding to the energy of first and second photons. A system of measurement of back scattered radiation is formed of a pulse-height discriminator and counting-rate meter, and there are provided two systems of measurement in the present example. The number of the systems is smaller by one than the kinds of the components to be measured.

In the apparatus for radiation analysis as structured above, a radiation having 59.5 KeV, 26.3 KeV, 17.8 KeV, etc. of energy of photons is emitted from the radiation source 1, but the discrimination range of each of the pulse-height discriminators 4a, 4b is set up in the present example to be responsive to photons having energy within a narrow energy range including the energy level of either 48.26 KeV or 23.85 KeV possessed by the back scattered photons, the back scattered photons corresponding to the incident photons whose energy is either 59.5 KeV or 26.3 KeV. Since, for the pulse-type radiation detector 2, a detector having half-width better than 10% is readily available, the power of the back scattered radiations having the above two energy levels can be measured separately by the use of a single detector. That is, the outputs of the first and second counting-rate meters 5a, 5b are in fact signals $I_{1,S}$ and $I_{2,S}$ proportional to the intensity of the first and second back scattered radiations, and thus the mass of hydrogen, carbon, and oxygen in a unit volume is obtained through the four-rule arithmetic computation as described above using the values of the above mentioned signals and the constants $\mu$ and $\rho$.

The four-rule arithmetic computation in this case can be carried out, similarly to the case of ordinary measurement of radiation intensity, according to equations (7), (8), and (9), in which:

$$\frac{I_{1,s}}{k_1 I_{1,0}} = P_1$$

$$\frac{I_{2,s}}{k_2 I_{2,0}} = P_2$$

$$\sigma_C(E_{1,0}) - P_1\{\mu_C(E_{1,0}) + \mu_C(E_{1,S})\} = a_{11}$$

$$\sigma_H(E_{1,0}) - P_1\{\mu_H(E_{1,0}) + \mu_H(E_{1,S})\} = a_{12}$$

$$\sigma_O(E_{1,0}) - P_1\{\mu_O(E_{1,0}) + \mu_O(E_{1,S})\} = a_{13}$$

$$\sigma_C(E_{2,0}) - P_2\{\mu_C(E_{2,0}) + \mu_C(E_{2,S})\} = a_{21}$$

$$\sigma_H(E_{2,0}) - P_2\{\mu_H(E_{2,0}) + \mu_H(E_{2,S})\} = a_{22}$$

$$\sigma_O(E_{2,0}) - P_2\{\mu_O(E_{2,0}) + \mu_O(E_{2,S})\} = a_{23}$$

where $k_1$, $k_2$ are constants, and $(I_{1,0})$, and $(I_{2,0})$ are intensity of incident radiations which can be preset.

$$\frac{\rho_H}{\rho} = \frac{\begin{vmatrix} a_{11} & a_{11} - a_{13} \\ a_{21} & a_{21} - a_{23} \end{vmatrix}}{\begin{vmatrix} a_{11} - a_{12} & a_{11} - a_{13} \\ a_{21} - a_{22} & a_{21} - a_{23} \end{vmatrix}} \quad (7)$$

$$\frac{\rho_O}{\rho} = \frac{\begin{vmatrix} a_{11} - a_{12} & a_{11} \\ a_{21} - a_{22} & a_{21} \end{vmatrix}}{\begin{vmatrix} a_{11} - a_{12} & a_{11} - a_{13} \\ a_{21} - a_{22} & a_{21} - a_{23} \end{vmatrix}} \quad (8)$$

$$\frac{\rho_C}{\rho} = 1 - \frac{\rho_H}{\rho} - \frac{\rho_O}{\rho} \quad (9)$$

In the case of analysis of the substance consisting of such elements as hydrogen, carbon, and oxygen, it was impossible to achieve the purpose by the use of the prior art method such as the fluorescent X-ray measurement, for example, since the energy of photons of the fluorescent X-ray is very low in that case. By the present invention, however, the energy of photon of the back scattered radiation is dependent on the energy of photon of the incident radiation and the energy of photon of the incident radiation can be freely selected. Therefore, the measurement with such elements having smaller atomic weights can be readily performed.

Although, in the above described embodiment, a common source of radiation, radiation detection, and amplifier were used for the two systems of measurement of back scattered radiation, separate ones may be used for the two systems of measurement. And, while $\gamma$-ray or X-ray of energy levels of 59.5 KeV and 26.3 KeV was advantageously employed, radiations of different energy levels from a different source of radiation may be employed. Further, though counting-rate meters were used for providing signals proportional to the intensity of radiations, counters for counting the number of pulses during a fixed period of time may be used instead. Although, in the case illustrated in the drawing, proportions of component elements in a unit volume were arranged to be output, it is naturally possible to adapt other values, or properties, that are derivable therefrom to be output by the analyzing apparatus.

Although, in the foregoing, the case where the embodiment was used for analysis of elements in a substance was described, the method according to the present invention can be applied to a mixture in which various substances are uniformly mixed, for which case, it will be apparent that the mass absorption coefficients and mass back scattering coefficients for elements are to be read as those for such substances.

As described so far, the systems for radiation measurement in the present invention have been structured for measurement of back scattered radiation, and therefore the advantage has been obtained that the mass of each element or substance can be provided by the use of the systems of measurement which are smaller in number by one than the kinds of the components.

What is claimed is:

1. In an apparatus for radiation analysis for measurement of mass of each of a plurality of components included in a substance to be measured, said apparatus for radiation analysis comprising:
   a source of radiation for irradiating the substance to be measured;
   systems of measurement smaller in number by one than the number of different kinds of components, for detecting intensity of back scattering produced in said substance to be measured due to the irradiation of said substance; and
   a processing unit for determining the mass of each of the components through execution of a predetermined four-rule arithmetic computation by the use of the intensity of back scattering provided by the output from said systems of measurement, as well as mass absorption coefficients for incident photons, mass back scattering coefficients for said incident photons, and mass absorption coefficients for back scattered photons, which are previously given coefficients relative to each of the components;
   each of the systems of measurement of back scattering being formed of a pulse-height discriminator for delivering output pulses of a given frequency at a predetermined level when pulse-height values of the signal indicating the intensity of the back scattering are within a predetermined range and a counting-rate meter for delivering an output at a level corresponding to the frequency of the output pulses of said pulse-height discriminator;
   said processing unit executing said four-rule arithmetic computation in accordance with the following equations $$\frac{\rho_1}{\rho} = \frac{\begin{vmatrix} a_{11} & a_{11} - a_{13} \\ a_{21} & a_{21} - a_{23} \end{vmatrix}}{\begin{vmatrix} a_{11} - a_{12} & a_{11} - a_{13} \\ a_{21} - a_{22} & a_{21} - a_{23} \end{vmatrix}}$$

$$\frac{\rho_2}{\rho} = \frac{\begin{vmatrix} a_{11} - a_{12} & a_{11} \\ a_{21} - a_{22} & a_{21} \end{vmatrix}}{\begin{vmatrix} a_{11} - a_{12} & a_{11} - a_{13} \\ a_{21} - a_{22} & a_{21} - a_{23} \end{vmatrix}}$$

$$\frac{\rho_3}{\rho} = 1 - \frac{\rho_1}{\rho} - \frac{\rho_2}{\rho}$$

where $\rho$ is the mass density of the substance
$\rho_1$ is the mass density of component 1
$\rho_2$ is the mass density of component 2
$\rho_3$ is the mass density of component 3.

2. An apparatus for radiation analysis according to claim 1, wherein said components are elements different from each another.

3. An apparatus for radiation analysis according to claim 1, wherein said components are compounds different from each another.

4. An apparatus for radiation analysis according to claim 1, wherein the number of components is three and the number of said systems of measurement of back scattering is two.

5. An apparatus for radiation analysis according to claim 4, wherein the components are carbon, hydrogen, and oxygen.

6. An apparatus for radiation analysis according to claim 1, wherein the ranges for energy discrimination by said pulse-height discriminators are set to narrow ranges including the energy level of either 48.26 KeV or 23.85 KeV.

7. An apparatus for radiation analysis according to claim 1, wherein said source of radiation is Am-241.

* * * * *

UNITED STATES PATENT AND TRADEMARK OFFICE
CERTIFICATE OF CORRECTION

PATENT NO. : 4,817,122

DATED : March 28, 1989

INVENTOR(S) : Shinji Badono et al.

It is certified that error appears in the above-identified patent and that said Letters Patent is hereby corrected as shown below:

Column 3, line 13, "component" should be --compound--;
           line 28, after "k" insert --$f$--.
Column 4, line 45 should read as follows:
--$\sigma_H(E_{1,0})$, $\sigma_H(E_{2,0})$, $\sigma_C(E_{1,0})$, $\sigma_C(E_{2,0})$, $\sigma_O(E_{1,0})$ and $\sigma_O$--.
Column 5, line 1, after "having" insert --a--;
           line 12, "$\rho$" should be --$\sigma$--;

Signed and Sealed this

Tenth Day of July, 1990

Attest:

HARRY F. MANBECK, JR.

*Attesting Officer*     *Commissioner of Patents and Trademarks*